United States Patent [19]

Wilson

[11] Patent Number: 4,582,053
[45] Date of Patent: Apr. 15, 1986

[54] ACOUSTIC EAR PLUG

[76] Inventor: Garnet J. E. Wilson, 8533 Hudson Dr., San Diego, Calif. 92119

[21] Appl. No.: 568,785

[22] Filed: Jan. 6, 1984

[51] Int. Cl.$^4$ .............................................. A61F 11/02
[52] U.S. Cl. ...................................... 128/152; 128/151
[58] Field of Search ................................. 128/151, 152

[56] References Cited

U.S. PATENT DOCUMENTS

| Re. 29,487 | 12/1977 | Gardner | 128/152 |
|---|---|---|---|
| 2,441,866 | 5/1948 | Cantor | 128/152 |
| 2,888,921 | 6/1959 | Nielson et al. | 128/151 |
| 3,131,241 | 4/1964 | Mendelson | 128/151 |
| 3,259,128 | 7/1966 | Leight | 128/152 |
| 3,881,570 | 5/1975 | Lewis | 128/152 |
| 4,089,332 | 5/1978 | Rose | 128/152 |
| 4,094,315 | 6/1978 | Leight | 128/152 |
| 4,314,553 | 2/1982 | Westerdal | 128/152 |

FOREIGN PATENT DOCUMENTS 225607 9/1910 Fed. Rep. of Germany ...... 128/152

Primary Examiner—Mark L. Bell
Attorney, Agent, or Firm—Gary, Juettner & Pyle

[57] ABSTRACT

An acoustic ear plug comprises, individually or in combination, a first element to be inserted within the ear canal and comprising an elongate hollow cylinder having a tapered forward insertion end and a pliant wall of acoustic barrier material on the forward portion and over the majority of the length of said cylinder, said wall being compressible and having compression recovery characteristics accommodating firm and conformable reception of the element deeply into the ear canal to completely block the canal over a significant axial distance, the rearward portion of the cylinder defining a stem facilitating insertion and removal of the element; and a second element to be inserted in and cover the outer ear and comprising a hollow bell of a size to cover the ear, an acoustic barrier wall on the outer surface of the bell, and a shape retaining but resilient ear piece on the forward portion of the bell accommodating firm and conformable reception of the ear piece in the outer ear to completely cover and block the ear canal, said ear piece including a tubular extension centrally thereof accommodating firm and conformable reception therein of the rearward portion of said cylinder and extension thereof into juxtaposition with the forward surface of the bell; said cylinder and said bell being evacuated and when used in combination acting in series to mitigate transmission of sound into the ear, said pliant wall and said ear piece mitigating transmission of sound into the ear around said cylinder and also dampening out vibrations imparted respectively to said cylinder and said bell for further mitigating transmission of sound into the ear.

16 Claims, 8-Drawing Figures

ACOUSTIC EAR PLUG

CROSS REFERENCE

The present application is based upon Disclosure Document No. 112499, filed Nov. 8, 1982.

BACKGROUND OF THE INVENTION

Ever since human beings subjected themselves to excessive noise, they have sought to protect themselves from the noise and to deaden or dull the transmission of the noise to the ear drum and human senses. All variety of devices have been stuffed in and hung over humans' ears to achieve the desired result—wads of cotton, fibrous plugs, stretchable envelopes with deformable fillers, acoustic barrier discs, thin walled resilient air filled chambers adapted to be forced into the ear canal, and various ear muffs and covers.

Ear muffs or covers designed to achieve the desired result must essentially be clamped to the head over the ears, usually by means of a bowed leaf spring connected to both covers and extending over the top of the user's head. Such covers tend to be very bulky and uncomfortable, causing the user physical irritation and distress. Consequently, considerable effort has been expended to develop ear plugs that can be inserted in the ear, either within the ear canal and/or within the folds of the outer ear to be comfortably supported by the ear itself without extraneous springs or other fastening devices.

Acoustic ear plugs tend to be very small in order to fit within the ear canal and/or outer ear and to be of sufficiently light weight as to be comfortably supported by the ear itself. Wads of cotton and other fibrous materials easily adapt to the structure of the ear and are light weight, but they provide relatively small acoustic barrier values. Thin walled resilient air filled chambers, such as shown in U.S. Pat. Nos. 3,259,128 to Leight and 4,089,332 to Rose, can easily be inserted in the ear canal and, due to their resiliency and internal pressure, will expand into and completely fill the recesses of the canal. Such devices have been reasonably successful and claim a noise reduction rating of 26 decibels.

Another approach to the subject, as disclosed in U.S. Pat. No. Re. 29,487 to Gardner, involves the use of an elongate cylindrical plug comprised of certain polymeric foam materials having sound barrier properties and also having compression recovery characteristics such that following compression for insertion into the ear canal the plug can slowly recover and expand into conformity with the interior structure of the canal and thereby establish substantially complete obturation.

While these proposals have provided certain advances in the art, it remains that ear plugs having even greater acoustic barrier capabilities are desired. For purposes of greater obturation of noise, it would seem that vacuum would be an ideal medium. However, based on the prior publications presently known, it would appear that evacuated chambers have not achieved acceptance in the acoustic ear plug art.

German Pat. No. 225,607, granted in 1910, discloses the use of an evacuated chamber in the formation of an acoustic ear plug. In two of the three illustrated embodiments (FIGS. 1 and 2), a spherical vacuum chamber is formed from a hard material and covered with an elastic material, which in the case of FIG. 2 is relatively thick and further provided with a cover. In the FIG. 3 embodiment, a spherical vacuum chamber is filled with cotton "to support the cover over the vacuum". The specification, which is very abbreviated, states that the sphere can be replaced with any anatomic shape, but contains no specifics. Presumably, this disclosure has not found acceptance in the art due to the need for a rigid or incollapsible vacuum chamber structure and a consequent inability to adapt such structure to the variable conformations of the human ear to seal off or substantially completely obturate the ear canal. The spherical chamber of the German patent appears most difficult to work with and the least susceptible to provision of both a vacuum chamber of effective size and at the same time sufficient spacial tolerance to accommodate an adequate body of elastic material capable of obturating the canal.

SUMMARY OF THE INVENTION

The present invention is directed to the effective and practical utilization of vacuum chambers in ear plug technology, both for ear canal applications and outer ear applications. In essence, the invention resides in the combination of an evacuated chamber of improved design and sufficient volume to provide highly effective obturation of sound and a relatively thin but quite voluminous exterior wall of a material that has good sound barrier properties, is readily compressible for ease of insertion in the ear, and has compression recovery characteristics facilitating reasonably precise conformation of a large volume of the material to the interior structure of the portion of the ear in which the ear plug is inserted.

For ear canal applications, the evacuated chamber is preferably an elongate hollow cylinder having a tapered forward or insertion end, and a main body portion of a length greater than the straight line accessible portions of the ear canal to provide a vacuum chamber of significant volume, and also an outwardly extending or rearward portion which defines a stem for manipulation of the ear plug. The forward portions and the majority of the length of the evacuated chamber member, i.e., except for a rearward stem portion thereof, are comprised of a compressible acoustic barrier material having good compression recovery characteristics, e.g., a relatively thin air filled envelope such as disclosed by Rose, or a material such as disclosed in the Gardner patent, whereby the vacuum chamber will obturate the major volume of the ear canal and the compressible acoustic barrier material will obturate, over a significantly long axial distance, the relatively narrow annular space between the chamber and the walls of the ear canal.

The resultant structure distinguishes over the German patent in that the elongate cylindrical member provides a vacuum chamber of far greater length and far greater volume, and thus far greater obturation capacity, than the chambers of the German patent, and at the same time a far greater capacity for a large volume of acoustic barrier material which, while of relatively thin radial section, is of significant length and thus capable of obturating the annular space between the vacuum chamber and the walls of the ear canal over a substantial axial distance. In contrast, the elastic covering of the spherical members of the German patent can have little if anything more than a single circular line of contact with the walls of the ear canal. Consequently, the present invention provides an ear plug of greatly enhanced sound barrier characteristics.

For outer ear applications, the concept is much the same, i.e., a large volume evacuated chamber associated with a relatively thin but nevertheless voluminous body of compressible, readily recoverable, acoustic barrier material readily adaptable to the conformations of the portion of the ear within which inserted.

In the preferred embodiment, an ear canal plug and an outer ear cover are combined and interconnected in series to provide the ultimate in sound obturation.

Other objects and advantages of the invention will become apparent from the following detailed description, as taken in conjunction with the accompanying drawings.

THE DRAWINGS

DETAILED DESCRIPTION

Figure 1:
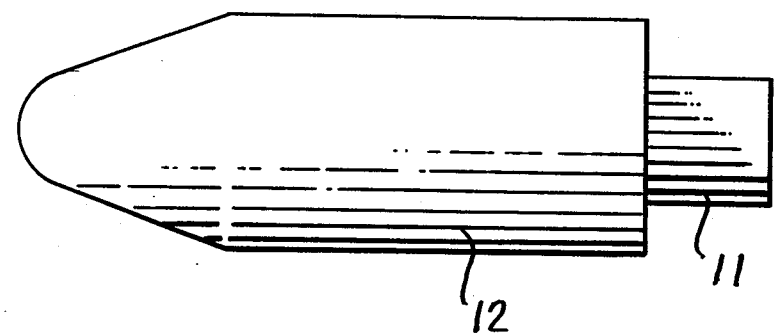
FIG. 1 is a view in side elevation of one embodiment of an acoustic ear plug for the ear canal.
Figure 2:
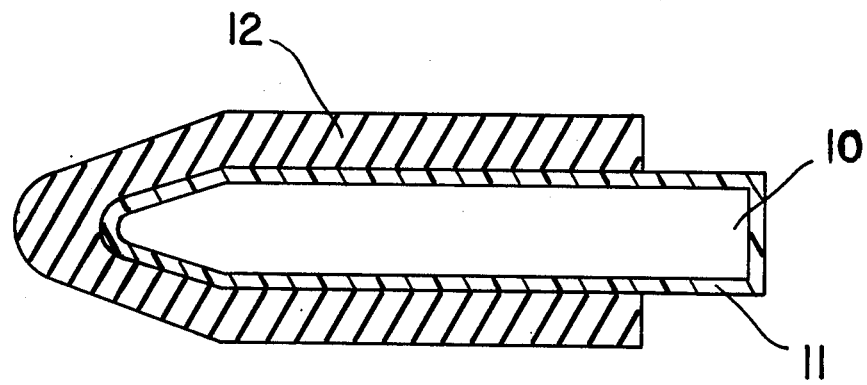
FIG. 2 is a longitudinal sectional view of the ear plug shown in FIG. 1.

Referring to FIGS. 1 and 2, an acoustic ear plug intended for insertion in the ear canal is shown as being comprised of an evacuated chamber 10 defined by and within an elongate hollow cylinder 11 of generally bullet shape having a tapered or conical forward or insertion end, and a pliant exterior wall 12 of acoustic barrier means on the forward portion and over the majority of the length of the cylinder 11.

In the embodiment of FIGS. 1 and 2, the cylinder member per se is of a diameter slightly smaller than the smallest diameter within the ear canal within which the plug is to be inserted and of a length significantly greater than the straight line accessible portions of such canal, so that the cylinder may be fully embedded in the canal and yet have the rearward portion thereof project outwardly of the ear canal to define a stem for manipulation of the ear plug to facilitate its insertion in and removal from the ear canal. The peripheral wall of the cylinder is as thick as need be to maintain the integrity of the cylinder under internal vacuum, but at the same time as thin as possible to mitigate transmission of noise via the wall itself. The forward end of the cylinder is preferably conical to facilitate insertion of the plug fully and deeply into the ear canal. The chamber 10 thus defined by the cylinder 11 is of significant volume and may be evacuated in any conventional manner to any degree of vacuum desired.

Figure 7:
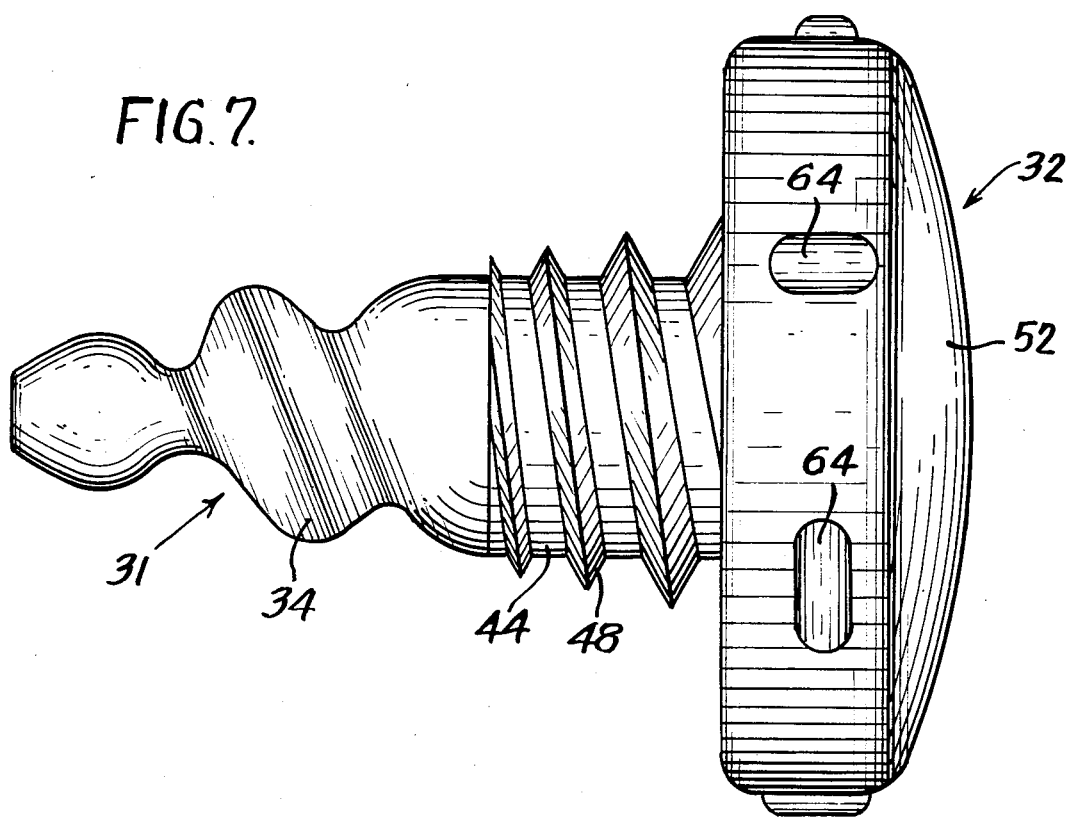
FIG. 7 is a side elevation of a preferred embodiment of acoustic ear plug comprising, in combination, a preferred ear plug for the ear canal and a preferred ear cover for the outer ear.

The peripheral wall of the cylindrical portion of the cylinder 11 is preferably somewhat flexible or compressible to provide for comfortable insertion of the plug into the ear canal, and at the same time has sufficient recovery characteristics for conformable reception of the plug in the canal, but not so flexible or compressible as to collapse under the forces of internal vacuum. To enhance flexibility, the peripheral wall may be formed as a series of circumferential undulations or as an auger, as shown in FIG. 7, whereby the cylinder may contract and expand longitudinally, and thus to a degree radially as well, to facilitate comfortable insertion in the ear. Also, such longitudinal flexibility permits expansion and contraction of the cylinder to absorb and cushion and thereby mitigate transmission to the inner ear of sound concussions such as produced by explosions.

To provide the flexibility thus desired, and also economy in manufacture, the cylinder may suitably be made from any appropriate plastic material known in the art. When made of plastic, the interior surfaces of the cylinder are preferably coated with an impervious barrier material, for example, a thin electro-plated layer of metal, to maintain the integrity of the internal vacuum chamber against degasification and/or leakage.

In the FIG. 1—FIG. 2 embodiment, wall 12 comprises a pliant covering extending over the forward portions and the majority of the length of the cylinder 11, at least over the entirety of the portion of the cylinder to be inserted into the ear canal. Preferably, a short section of the rear of the cylinder is left uncovered to provide a stem for manipulation of the plug. The pliant covering is selected from a group of suitable barrier means that have good acoustic barrier properties, adequate compressibility to facilitate insertion in the ear, and sufficient compression recovery characteristics to expand into the interior configurations of the ear canal and completely obturate the canal within a short time after the plug is inserted in the ear. Suitable materials or means include polymeric foam materials such as described in the Gardner U.S. Pat. No. Re. 29,487, as shown in FIG. 2; and a thin-walled, resilient, air-filled, annular chamber constructed somewhat as shown in the Rose U.S. Pat. No. 4,089,332, but mounted in annularly encircling relation to the cylinder 11 as indicated by the marginal outline of the material 12 in FIG. 2.

The pliant acoustic barrier 12, while of relatively thin radial section in order to accommodate the largest possible vacuum chamber, is of significant axial dimension in order to provide a large volume of acoustic barrier material in the annular space between the evacuated cylinder and the interior walls of the ear canal, thereby to completely obturate the ear canal. Also in this embodiment, the barrier wall 12 serves to isolate the cylinder 11 from direct contact with the structure of the ear and thereby dampen out the transmission to the inner ear of any vibrations that may be imparted to the cylinder 11 by acoustic shock or otherwise.

The resultant structure provides a vacuum chamber of relatively great length and large volume for insertion in the ear canal to mitigate transmission of sound to the inner ear and the human senses. At the same time, the evacuated cylinder accommodates a large volume of compressible, compliant, acoustic barrier material for effectively dampening out vibrations and fully obturating the annular space between the vacuum chamber and the walls of the ear canal over a substantial axial distance. Thus, the present invention provides an improved ear plug of greatly enhanced sound reduction capacity.

Figure 3:
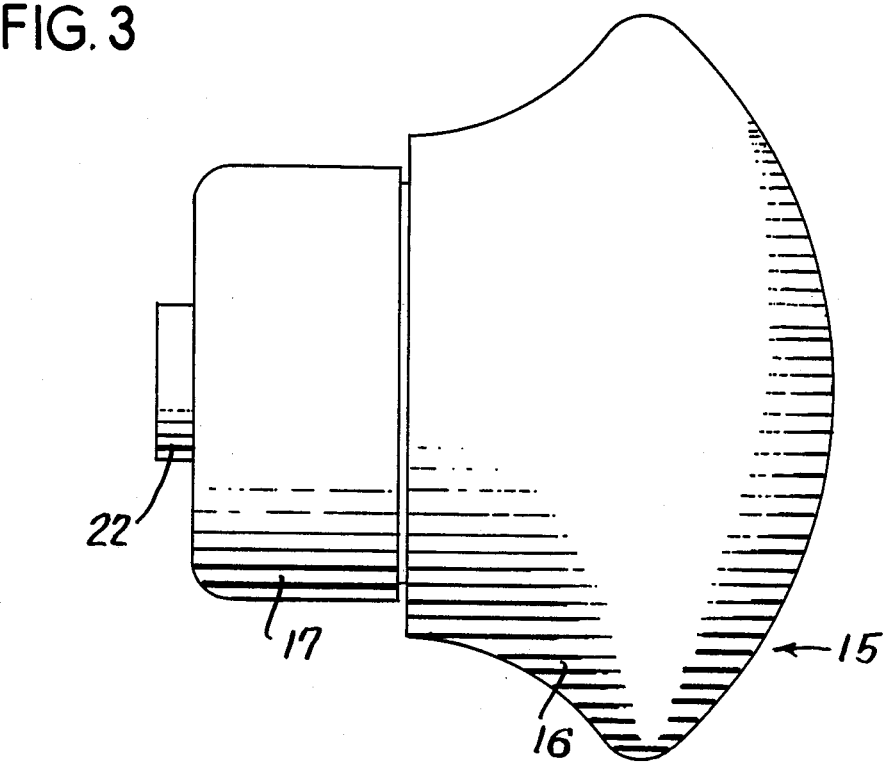
FIG. 3 is a view in side elevation of one embodiment of an acoustic ear plug for the outer ear.
Figure 4:
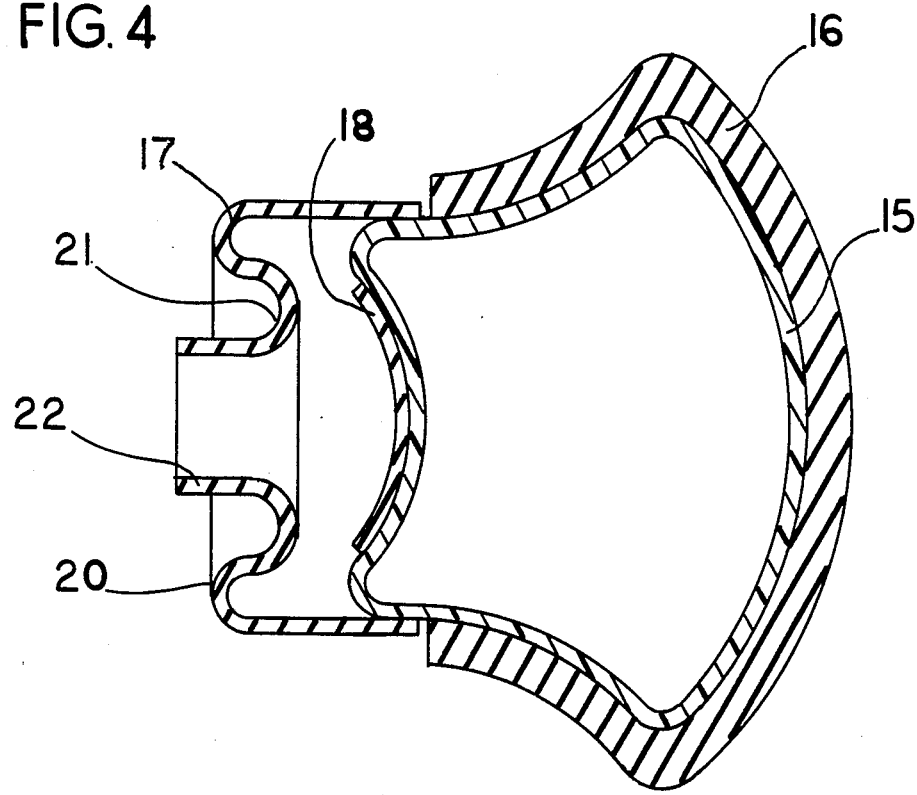
FIG. 4 is a longitudinal sectional view of the ear plug shown in FIG. 3.

Referring now to FIGS. 3 and 4, an acoustic ear plug or cover intended for mounting in the outer ear, and embodying much of the same technology as above described, is shown as comprising in essence, an evacuated bell 15 having an acoustic barrier covering 16, and a collar 17 for mounting the bell in the outer ear in overlying relation to the ear.

The evacuated bell 15 may take any of a variety of configurations. Preferably, the same is generally cylindrical and tapered outwardly from its inner to its outer ends, and provided with a convex outer end wall and a concave inner end wall, thereby to take on a shape similar to a bell. The walls of the bell are sufficiently thick to maintain the integrity of the bell shape under internal vacuum and when being manually manipulated by the user. Otherwise, the walls are preferably as thin as they may practically be formed to mitigate transmission of noise and and/or vibrations via the walls themselves. If the bell is formed of plastic, the internal surfaces thereof are preferably coated with a gas impervious barrier layer to mitigate against degasification and/or leakage. The hollow chamber thus defined within the bell is of large volume and may be evacuated in any conventional manner to any degree of vacuum desired.

The outer surfaces of the bell are covered by acoustic barrier means including an integral acoustic cover 16 on the side and outer end walls of the bell, the collar 17 encircling the portion of the side wall adjacent the inner end wall, and an acoustic pad 18 on the inner end wall. In this ear plug, the cover 16 and pad 18 may be formed of any material desired to define a soft and decorative covering on the bell, but preferred materials are acoustic foam materials such as described in the Gardner U.S. Pat. No. Re. 29,487.

The collar 17 serves to mount the bell on the ear by insertion of the same into the convolutions of the ear. To this end, the collar is formed of a resilient but nevertheless shape-retaining or form-holding material such a rubber or synthetic rubber, or acoustic barrier materials with compressive memory characteristics as described in the Gardner Reissue patent. To fit within the outer ear, the collar includes an inwardly facing annular rib 20 surrounding an annular recess 21 which in turn surrounds a central plug means 22 adapted to overlie and be received in the outer portions of the ear canal. By virtue of the protrusions that fit within the convolutions of the ear, i.e., the rib 20 and plug 22, and the compression recovery characteristics of the material from which they are formed, the bell is firmly but comfortably mounted on the ear with sufficient adherence that the user may move about and participate in various physical activities without displacing the ear plug from the ear. Also, the tubular walls defined by the collar and the central plug thereof serve as shock-absorbers to prevent physical contact between the bell and the ear and to dampen out any vibrations that may be imparted to the bell by physical contact, acoustic shock, or otherwise.

Thus, the present invention provides an acoustic outer ear plug, as well as an ear canal plug, characterized by a large volume evacuated chamber and a compliant acoustic barrier material coupling the chamber to the structure of the ear for effectively dampening out vibrations and fully obturating the ear canal primarily by the evacuated chamber. In this manner, the invention provides improved acoustic ear plugs attaining greatly enhanced sound reduction capacities.

Figure 5:
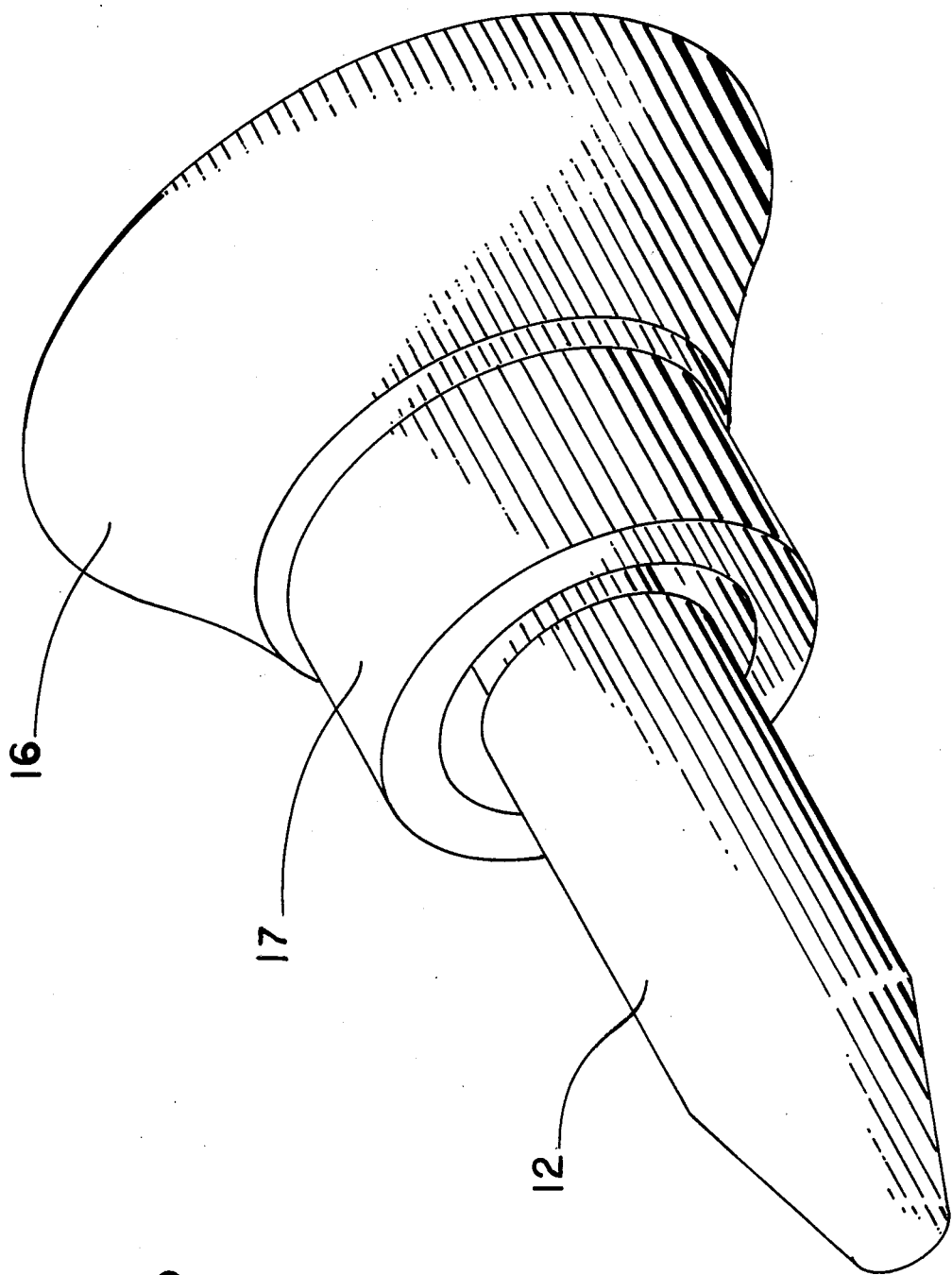
FIG. 5 is a perspective view of a combination ear plug comprised of the ear plugs of FIGS. 1 and 3 connected together so as to act in series.
Figure 6:
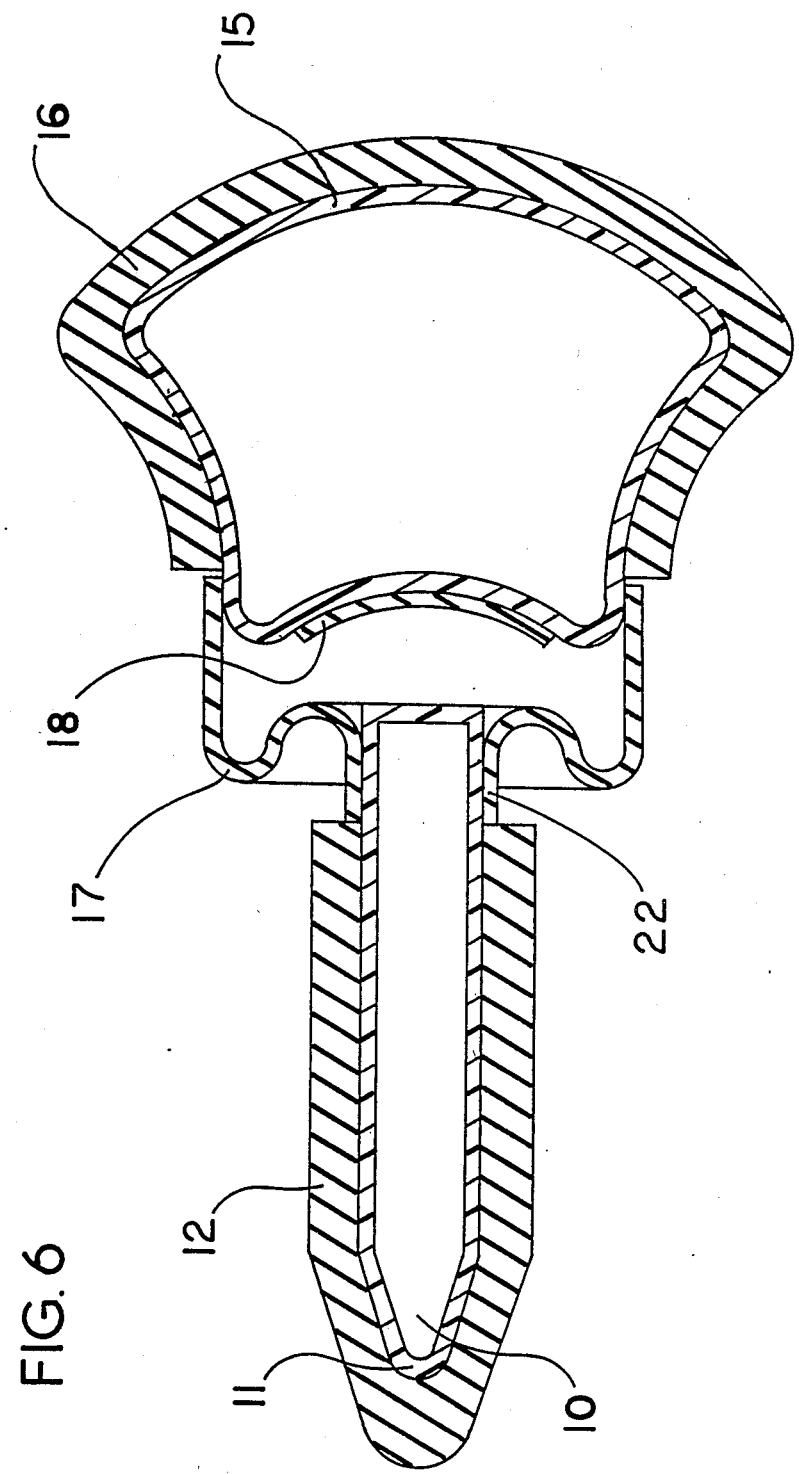
FIG. 6 is a longitudinal sectional view of the combination ear plug shown in FIG. 5.

The ear canal plug of FIGS. 1 and 2 and the outer ear plug of FIGS. 3 and 4 may be used individually and independently as is apparent from the foregoing description. However, the same are specifically devised for use in combination with one another, whereby the ultimate in sound obturation may be conveniently and effectively achieved. For the purpose, the collar 17 and the central plug portion 22 thereof preferably are hollow, as shown in FIG. 6, and the plug 22 has an inner diameter approximately equal to the outer diameter of the rearward stem portion of the cylinder 11, whereby the plug may be mounted in part on the cylinder and whereby the rearward end of the cylinder may project into the collar 17 into juxtaposition with the concave inner end wall of the bell 15. The completed assembly of the combination is shown in FIGS. 5 and 6. In the combination, the two evacuated chambers act in series with one another to provide maximum sound obturation, and the various pliant, acoustic barrier materials, especially the wall 12, the collar 17 and the pad 18, prevent transmission of sound and/or vibrations from the bell to the cylinder, and from the cylinder to the inner ear and the human senses.

Figure 8:
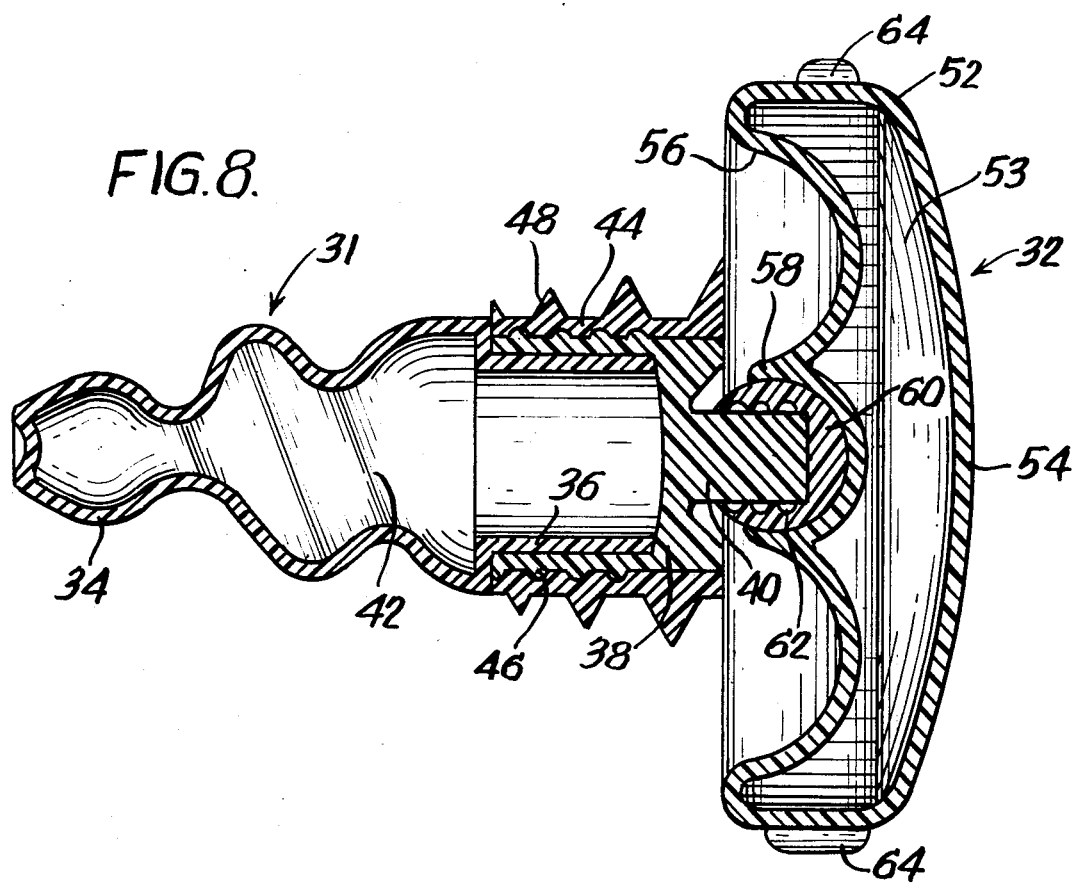
FIG. 8 is a longitudinal sectional view of the combination acoustic ear plug shown in FIG. 7.

Referring to FIGS. 7 and 8, a modified and preferred form of ear plug is shown as comprising a first element 31 for insertion in the ear canal and a second element 32 for mounting in and over the outer ear, the two elements being usable individually or in combination.

The first element 31 comprises a hollow cylinder member 34 that is molded or otherwise formed from a shape or form retaining material that is compressible, has a good compression recovery characteristic irrespective of internal vacuum forces, and has acoustic barrier properties, such as materials of the type described in the Gardner reissue patent. The interior surfaces are preferably coated with a gas impervious layer as previously described. The main body portion of the cylinder 34 is generally tapered from its forward insertion end rearwardly outwardly to its stem end, and the peripheral wall thereof is preferable undulating and molded in the form of a continuous auger thread. At its rearward or stem end, the cylinder wall terminates in a tubular portion 36 which is received within and welded or otherwise permanently affixed to a substantially rigid stem 38 having a rearwardly projecting finger grip portion or extension 40 facilitating manipulation of the plug. The stem 38 is generally cylindrical and hollow so that it and the cylinder member 34 together define a vacuum chamber 42 of relatively large volume. This chamber is evacuated in any conventional manner to any degree of vacuum desired. Surrounding the body portion of the stem 38 is a covering wall 44 of acoustic barrier material which is preferably connected to the stem by a threaded connection 46 and which itself has an exterior surface in the form of a screw thread 48. The thread 48 is preferably tapered, rearwardly outward, commencing with a minor diameter approximately equal to the major dimension of the cylinder 34.

In use, the ear canal plug 31 may be inserted in the ear canal by first compressing the cylinder member 34 and inserting it into the ear canal, and then rotating the plug by means of the stem 40 so that the threads defined on the cylinder 34 and the barrier wall 44 aid in pulling the plug fully into the ear canal. To prevent damage to the ear drum, the forward end of the cylinder 34 is blunt and readily compressible. To maintain the plug spaced from the ear drum in actual use, the threaded connection 46 between the wall 44 and the stem 38 accommodates a degree of adjustment of the overall length of the plug to adapt the same to the ears of various individual users.

Thus, the ear plug element 31 assures obturation of the ear canal and effective acoustic protection of the ear by virtue of a vacuum chamber of large effective volume and acoustic barrier material, also of large effective volume, capable of compressive recovery for expansion into intimate conformity with the walls of the ear canal over a significant axial distance.

To enhance the protection for the ear, or as an alternative form of protection for the ear, the invention also provides an outer ear plug or cover comprising the second element 32. The element 32 is formed in principal part by a hollow bell 52 of a size to cover all or the majority of the outer ear, and defining a vacuum chamber 53. The bell has a convex outer wall 54 which acts as a drum for absorbing concussive shocks such as produced by explosions. The inner wall 56 of the bell may be concave and shaped much as described in connection with the embodiment of the invention shown in FIG. 4 to facilitate mounting of the bell within the folds of the outer ear. Also, the inner wall of the bell includes a tubular portion 58 which may be fitted into the outer end of the ear canal to mount the bell on and over the outer ear.

For purposes of use in combination with the ear canal plug element 31, the tubular portion 58 of the inner wall of the bell is formed as a resilient spherical socket for detachable reception therein of a ball 60, the ball 60 having a recess therein for detachable mounting on the stem extension 40 of the element 31. The connection between the stem 40 and the ball 60 is preferably adjustable by means of a cooperative push-pull detent system 62. The adjustments thus accommodated by the detent system 62 and the ball and socket system 58-60 assures optimum fit of both of the elements 31 and 32 within the ears of various individual users.

The bell 52 is preferably constructed in essentially the same manner and from the same materials as the other acoustic elements of the invention and is preferably provided on its peripheral surface with alternating lugs 64 facilitating axial movement and rotation of the plugs upon insertion of the same into and removal of the same from the user's ear.

In the combination shown in FIGS. 7 and 8, the two evacuated chambers 42 and 53 act in series to provide maximum sound obturation and concussive shock absorption, and the pliant acoustic barrier materials used in their construction prevent transmission of sound and/or vibrations to the inner ear and the human senses.

Thus, practical modes of thoroughly effective use of evacuated chambers have been disclosed for use in the acoustic ear plug art; and the objects and advantages of the invention have been shown to be attained in a practical, effective, efficient and economical manner.

While certain preferred embodiments of the acoustic ear plug of the invention have been illustrated and described herein, it is to be appreciated that various changes, rearrangements and modifications may be made therein without departing from the scope of the invention, as defined by the appended claims.

What is claimed is:

1. An acoustic ear plug comprising a unitary element to be inserted within the ear canal and comprising an elongate hollow cylinder having a tapered forward insertion end and a pliant external wall of acoustic barrier material on the forward portion and over the majority of the length of said cylinder, said wall being compressible and having compression recovery characteristics accommodating firm and conformable reception of the element deeply into the ear canal to completely block the canal over a significant axial distance, the rearward portion of the cylinder defining a stem faciliating insertion and removal of the element; said cylinder being evacuated and comprising a vacuum chamber of large effective volume for obturating the major volume of the ear canal and significantly mitigating transmission of sound into the ear, said pliant wall mitigating transmission of sound into the ear around said cylinder for further mitigating transmission of sound into the ear.

2. An acoustic ear plug as set forth in claim 1, wherein said cylinder is formed of plastic and the internal surfaces thereof are coated with a layer of gas barrier material to provide a gas impervious vacuum chamber.

3. An acoustic ear plug as set forth in claim 1, wherein said hollow cylinder comprises a generally bullet shaped element of a length greater than the axial dimension of the ear canal and said pliant external wall comprises a covering on the forward portion and over the majority of the length thereof.

4. An acoustic ear plug as set forth in claim 1, wherein said hollow cylinder is formed in part by said pliant external wall and in further part by said stem, said stem and wall being joined together and defining a large volume vacuum chamber therein.

5. An acoustic ear plug as set forth in claim 4, wherein said pliant external wall comprises a series of undulations.

6. An acoustic ear plug as set forth in claim 4, wherein said pliant external wall is undulating and in the form of an auger thread and said stem has a pliant external wall covering in the form of a screw thread.

7. An acoustic ear plug as set forth in claim 6, including means on said stem and said external covering therefor accommodating axial adjustment therebetween and thus between said auger thread and said screw thread to vary the overall length of the plug.

8. An acoustic ear plug comprising a unitary element to be inserted in and cover the outer ear and comprising a hollow bell of a size to cover the ear, an acoustic barrier wall on the outer surface of the bell, and a shape retaining but resilient earpiece on the forward portion of the bell accommodating firm and conformable reception of the earpiece in the outer ear to completely cover and block the ear canal; said bell being evacuated and comprising a vacuum chamber of large effective volume covering the ear for significantly mitigating transmission of sound into the ear, said earpiece mitigating transmission of sound into the ear around said bell and also dampening out vibrations imparted to said bell for further mitigating transmission of sound into the ear.

9. An acoustic ear plug as set forth in claim 8, wherein said earpiece includes an axial extension for insertion in the outer end of the ear canal to retain the ear plug on the user's ear.

10. An acoustic ear plug as set forth in claim 8, including a resilient tubular collar extending between and connecting said earpiece to said bell, said resilient tubular collar dampening out vibrations imparted to said bell.

11. An acoustic ear plug as set forth in claim 8, said bell having an outwardly bowed outer wall forming a drum wall for absorbing concussive shocks.

12. An acoustic ear plug comprising, in combination:
a first element to be inserted within the ear canal and comprising a hollow cylinder having a pliant external wall of acoustic barrier material on the forward portion and over the majority of the length of said cylinder, said wall being compressible and having compression recovery characteristics accommodating firm and conformable reception of the element in the ear canal, the rearward portion of the cylinder defining a stem facilitating insertion and removal of the element, said cylinder being evacuated and comprising a vacuum chamber of large effective volume for obturating the major volume of the ear canal; and a second element to be inserted in and cover the outer ear and comprising a hollow bell of a size to cover the ear, said bell being evacuated and comprising a vacuum chamber of large effective volume covering the outer ear, an acoustic barrier wall on the outer surface of the bell, a shape retaining but resilient earpiece on the forward portion of the bell accommodating firm and conformable reception of the earpiece in the outer ear, and an extension on the earpiece accommodating firm and conformable reception of said stem to interconnect said first and second elements;

said vacuum chambers in said cylinder and said bell acting in series for significantly mitigating transmission of sound into the ear.

13. An acoustic ear plug as set forth in claim 12, wherein said extension on said earpiece is hollow and said stem extends therethrough into juxtaposition with the forward surface of said bell, said forward surface of said bell having an acoustic pad thereon juxtaposed to said stem.

14. An acoustic ear plug as set forth in claim 12, wherein said extension on said earpiece comprises a spherical socket, a ball mounted in said socket for swivel movement therein, and a recess in said ball for reception of said stem for interconnecting said first and second elements and accommodating individual adjustment of the two elements to the ear and ear canal of the user.

15. An acoustic ear plug as set forth in claim 14, including means on said stem and said ball for adjusting the positions of the stem and ball axially relative to one another.

16. An acoustic ear plug as set forth in claim 1, wherein said pliant external wall is in the form of an auger thread so that the ear plug can be threadedly inserted in the ear and will pull itself fully into the ear canal.

* * * * *